(12) United States Patent
DeSantis

(10) Patent No.: US 8,002,796 B2
(45) Date of Patent: Aug. 23, 2011

(54) SURGICAL SUTURE NEEDLE WITH BLUNT SPHERICAL REGION

(75) Inventor: Robert J. DeSantis, West Redding, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 169 days.

(21) Appl. No.: 11/048,352

(22) Filed: Feb. 1, 2005

(65) Prior Publication Data

US 2005/0182446 A1 Aug. 18, 2005

Related U.S. Application Data

(60) Provisional application No. 60/544,288, filed on Feb. 12, 2004.

(51) Int. Cl.
*A61B 17/06* (2006.01)

(52) U.S. Cl. ......... 606/222; 606/223; 606/224; 604/264

(58) Field of Classification Search .......... 606/222–224; 604/264, 266, 268, 270, 272, 274
See application file for complete search history.

(56) References Cited

U.S. PATENT DOCUMENTS

| | | | | |
|---|---|---|---|---|
| 3,238,942 A * | 3/1966 | Lincoff | ......................... | 606/223 |
| 3,636,955 A | 1/1972 | Kurtz | | |
| 4,685,904 A * | 8/1987 | Krebs | ...................... | 604/164.06 |
| 4,776,847 A * | 10/1988 | Krebs | ...................... | 604/164.06 |
| 4,790,830 A * | 12/1988 | Hamacher | .................... | 604/274 |
| 4,799,484 A * | 1/1989 | Smith et al. | .................... | 606/223 |
| 4,966,143 A * | 10/1990 | Meinershagen | .............. | 606/103 |
| 5,053,047 A * | 10/1991 | Yoon | ............................. | 606/223 |
| 5,100,390 A * | 3/1992 | Lubeck et al. | ................ | 604/158 |
| 5,123,910 A * | 6/1992 | McIntosh | ...................... | 606/223 |
| 5,342,397 A * | 8/1994 | Guido | ........................... | 606/222 |
| 5,383,901 A * | 1/1995 | McGregor et al. | ............ | 606/223 |
| 5,403,344 A * | 4/1995 | Allen | ............................ | 606/223 |
| 5,464,422 A * | 11/1995 | Silverman | ..................... | 606/223 |
| 5,476,480 A * | 12/1995 | Matsutani et al. | ............ | 606/222 |
| 5,478,327 A * | 12/1995 | McGregor et al. | ............ | 604/272 |
| 5,609,604 A * | 3/1997 | Schwemberger et al. | .... | 606/185 |
| 5,665,078 A * | 9/1997 | McGregor et al. | ............ | 604/272 |
| 5,683,417 A * | 11/1997 | Cooper | ......................... | 606/223 |
| 5,693,072 A * | 12/1997 | McIntosh | ...................... | 606/223 |
| 5,797,961 A * | 8/1998 | Smith et al. | .................... | 606/222 |
| 5,913,875 A * | 6/1999 | Smith et al. | .................... | 606/222 |
| 5,964,765 A * | 10/1999 | Fenton et al. | .................. | 606/232 |
| 7,063,716 B2 * | 6/2006 | Cunningham | ................ | 606/222 |
| 7,338,502 B2 * | 3/2008 | Rosenblatt | .................... | 606/139 |
| 2004/0186515 A1* | 9/2004 | Rosenblatt | .................... | 606/228 |

FOREIGN PATENT DOCUMENTS

| | | |
|---|---|---|
| EP | 0494 648 A2 | 7/1992 |
| EP | 0500 229 A1 | 8/1992 |
| EP | 0619 983 A2 | 10/1994 |
| EP | 0648 473 A1 | 4/1995 |

OTHER PUBLICATIONS

European Search Report dated Jul. 1, 2010 for copending Appln. No. 05712329.1.

* cited by examiner

*Primary Examiner* — Darwin P Erezo
*Assistant Examiner* — Mark Mashack

(57) ABSTRACT

A surgical needle includes a needle body defining leading and trailing ends, a general spherical region disposed adjacent the leading end of the needle body and having a blunt outer surface, and a plurality of cutting edges extending from the spherical region toward the trailing end of the needle body.

11 Claims, 3 Drawing Sheets

SURGICAL SUTURE NEEDLE WITH BLUNT SPHERICAL REGION

CROSS REFERENCE TO RELATED APPLICATIONS

The present application claims priority of U.S. Provisional Patent Application Serial No. 60/544,288, filed on Feb. 12, 2004. The priority of this prior application is expressly claimed and the disclosure of which are hereby incorporated by reference in its entirety

BACKGROUND

1. Technical Field

The present disclosure relates to a surgical suturing needle for suturing cutaneous and subcutaneous tissue, and in particular, relates to a surgical needle including a blunt needle end for minimizing undesired or inadvertent penetration of tissue while also possessing cutting edges extending from the blunt needle end to provide penetration capabilities comparable to conventional pointed surgical needles.

2. Background of Related Art

Suturing needles for applying sutures, or stitches, by hand in cutaneous and sub-cutaneous tissue are well known in the art. Typically, the suturing needles are used to close wounds or adjoin adjacent tissue, often at the conclusion of a surgical procedure. Suturing needles are usually made from a cut blank of material such as stainless steel. The cut blank is metal-worked using well known machining techniques to form the suturing needle. The needle generally includes a shaft, a rear end portion with an aperture or channel to secure a suture thread and a needle head at a front end portion for puncturing skin and passing through tissue. The needle head typically incorporates a sharpened needle tip at its distal end and cutting edges. Alternatively, the needle tip may be of a tapered configuration. Straight and curved needles including multiple curved configurations are also known in the art.

Conventional suture needles typically incorporate an extremely sharpened needle end. Sharper needles require less force to penetrate tissue and thus cause less tissue trauma. In addition, a sharper needle reduces fatigue on the needle itself, making it less likely to bend or break during suturing. Needle sharpness is typically defined in terms of "penetration force"—the force necessary for a needle to puncture, or penetrate, the tissue. The penetration force is primarily determined by the design and sharpness of the needle point and the cutting edges formed on the needle head. Needle sharpness is also affected by drag force on the needle as it travels through the tissue. The drag force also depends upon the design and sharpness of the needle, and the presence of a lubricating coating.

However, sharper needles also increase the potential for inadvertent penetrating of neighboring healthy tissue and/or sticking of operating room personnel, their gloves, etc. To address these concerns, blunt surgical needles have been proposed. These surgical needles are generally of the taper-point design gradually tapering to a blunt needle end. However, these blunt taper point needles are devoid of cutting edges which detract from their usefulness in suturing tissue where relatively high penetration and drag forces are required to accomplish each needle pass.

SUMMARY

Accordingly, the present disclosure is directed to further advancements in surgical suturing needles. In one preferred embodiment, the surgical needle includes a needle body including leading and trailing ends and defining a longitudinal axis, a needle tip disposed adjacent the leading end of the needle body and having a blunt outer surface defining an arcuate configuration and at least one cutting edge extending from the needle tip toward the trailing end of the needle body. Preferably, the needle tip defines a circular cross-sectional dimension and may define a general spherical configuration. Alternatively, the needle tip may define a general elliptical cross-sectional dimension.

Preferably, the needle body includes a plurality (e.g., at least four) of cutting edges extending from the needle tip toward the needle body. Planar surface portions are disposed between adjacent cutting edges. Alternatively, the needle body includes concave surface portions disposed between and forming the cutting edges.

The needle body preferably defines an outer extent adjacent leading ends of the cutting edges substantially dimensionally equivalent to an outer periphery of the blunt outer surface of the needle tip. In this regard, the leading ends of the cutting edges do not extend beyond the periphery of the needle tip. This feature significantly reduces the potential of tissue snagging on the leading ends of the cutting edges during a pass through tissue. Alternatively, the outer extent of the needle body inclusive of the leading ends may be greater than an outer periphery of the blunt outer surface of the needle tip.

In another preferred embodiment, the surgical needle includes a needle body defining leading and trailing ends, a general spherical region disposed adjacent the leading end of the needle body and having a blunt outer surface, and a plurality of cutting edges extending from the spherical region toward the trailing end of the needle body.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

BRIEF DESCRIPTION OF PREFERRED EMBODIMENTS

Figure 1:
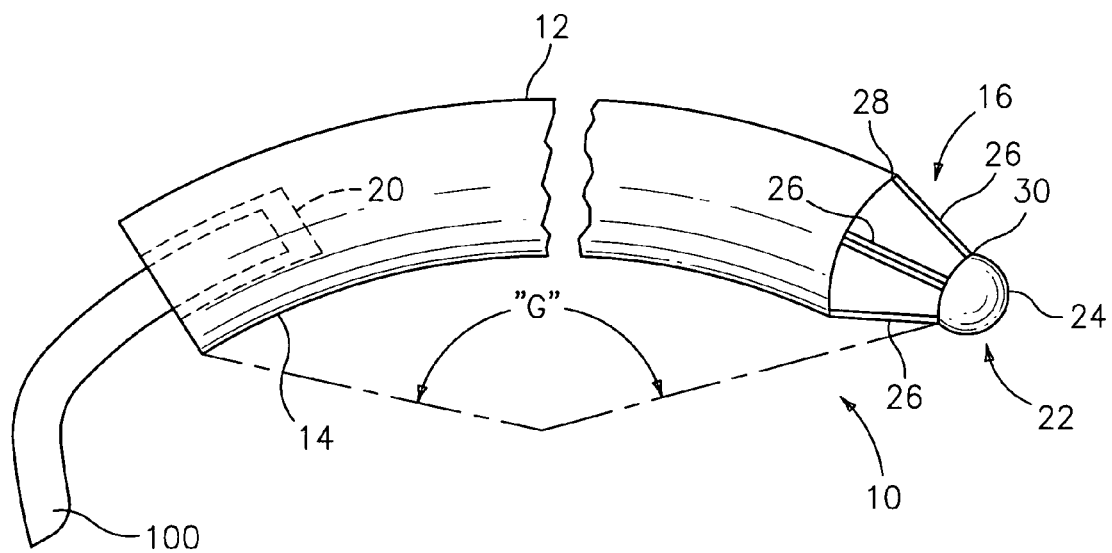
FIG. 1 is a side elevational view of the surgical needle in accordance with the principles of the present disclosure.

Preferred embodiment(s) of the surgical needle of the present disclosure will now be described in detail with reference to the drawings wherein like reference numerals identify similar or like elements throughout the several views.

Figure 2:
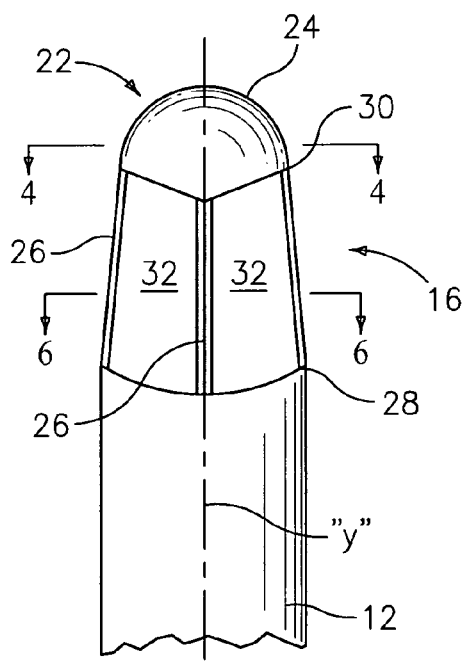
FIG. 2 is a side plan view of the needle end of the surgical needle of FIG. 1.
Figure 3:
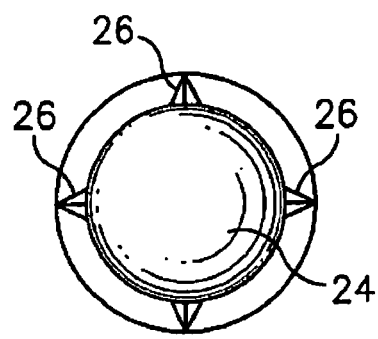
FIG. 3 is an axial view of the needle end.
Figure 4:
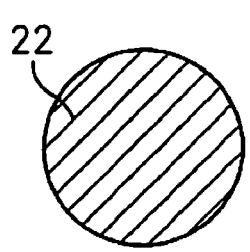
FIG. 4 is a cross-sectional view of the needle end of the surgical needle taken along the lines 4-4 of FIG. 2.

With reference now to FIG. 1, the surgical needle 10 of the present disclosure is illustrated. Surgical needle 10 includes elongated needle body 12 having rear or trailing end 14 and forward or leading needle end 16. Needle body 12 is curved along its length through an arc "G" ranging from about 90° to about 180°. Various angles of curvature are also envisioned. It is also contemplated that needle body 12 may be straight. As depicted in FIG. 2, needle body 12 defines longitudinal axis "y" which extends along the length of needle body 12.

With particular reference to FIG. 1 trailing end 14 of needle body 12 defines a circular channel 20 (shown in phantom) dimensioned for reception of a suture end of a suture 100. Channel 20 is closed about the suture end through conventional swaging or crimping processes to secure the suture 100 to elongated needle body 12. The dimensioning of channel 20 of trailing end 14 may be selected to provide for permanent (non-detachable) or detachable securement of the suture to needle body 12. The type of securement effectuated is also dependent upon the swaging force employed during the attachment process. Channel 20 may be formed with a conventional laser drilling process or the like. It is further envisioned that trailing end 14 may be provided with an open u-shaped channel, an eyelet etc. for receiving the suture end. Adhesive suture attachment methodologies are also envisioned where trailing end 14 is devoid of an opening or channel.

Figure 5:
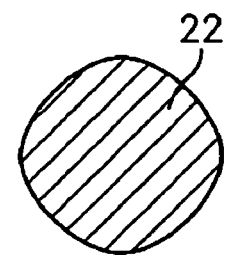
FIG. 5 is a cross-sectional view similar to FIG. 4 illustrating an alternate embodiment of the needle end.

Referring now to FIGS. 2-6, in conjunction with FIG. 1, needled end 16 will be discussed in detail. Needled end 16 includes needle tip 22, which in a preferred embodiment, defines a bulbous or spherical configuration having an arcuate outer surface 24. This spherical region of needle tip 22 provides a relatively enlarged and consequently blunted profile to needle 10 to minimize the potential of inadvertent or undesired sticking, pricking, etc. of a surgeon, surgeon's gloves or adjacent patient tissue area. Needle tip 22 may be in the form of a true spherical portion having a circular cross-section (FIG. 4) or alternatively may be an ellipsoid with an elliptical cross-section (FIG. 5). An elliptical arrangement may be desired in instances where a reduced needle profile is required to, e.g., minimize the penetration force associated with entering and passing through the tissue. Needle tip 22 is devoid of any sharpened edges and/or planar surfaces which would otherwise undesirably alter the blunt characteristic and functionality of the needle tip 22.

Figure 6:
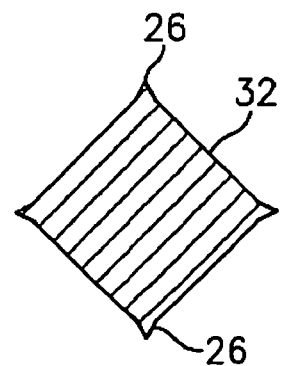
FIG. 6 is a cross-sectional view of the needle end of the surgical needle taken along the lines 6-6 of FIG. 1.

Needle body 12 further includes a plurality of cutting edges 26 which extend from needle tip 22 toward trailing end 14 of needle body 12. Preferably, four cutting edges 26 are provided, however, more or less than four cutting edges 26 are also contemplated. Cutting edges 26 extend in a general longitudinal direction relative to longitudinal axis "y" and terminate at an intermediate portion 28 of needle body 12. Cutting edges 26 gradually taper outwardly toward trailing end 14 at an angle ranging from about 1° to about 10° relative to the longitudinal axis. Cutting edges 26 are preferably triangular in cross-section as depicted in FIG. 6.

Figure 7:
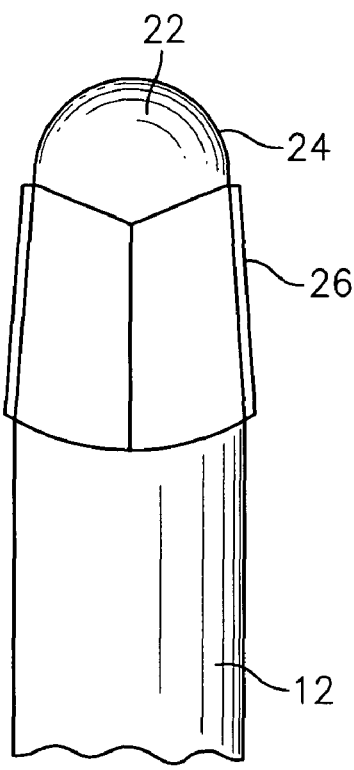
FIG. 7 is a side plan view of another alternate embodiment of the surgical needle of FIG. 1.

Cutting edges 26 define an effective lateral or radial extent at their leading ends 30 adjacent needle tip 22 substantially equivalent to the radial extent, i.e., diameter of needle tip 22. In particular, leading ends 30 of cutting edges 26 do not extend radially beyond the periphery of needle tip 22 as best depicted in FIG. 2. With this arrangement, a smooth transition is effected from needle tip 22 to cutting edges 26 thus minimizing the potential of tissue snag when leading ends 30 of the cutting edges 26 engage the tissue. Alternatively, cutting edges 26 may be dimensioned to extend beyond the diameter of needle tip as depicted in the embodiment of FIG. 7.

Figure 8:
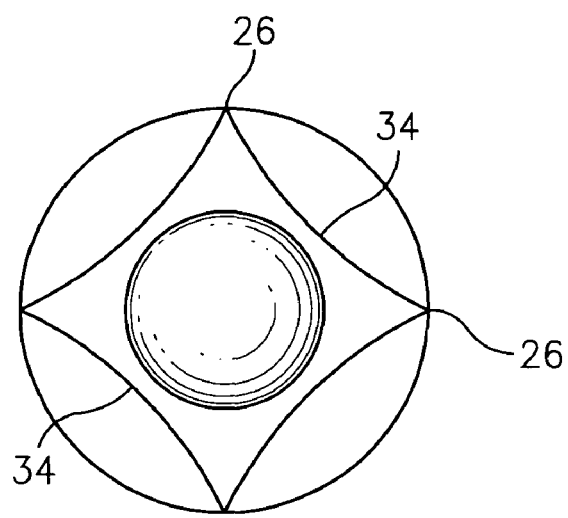
FIG. 8 is an axial view of an alternative embodiment of the surgical needle of FIG. 1.

Referring again to FIGS. 1, 2 and 6, needle body 12 further includes planar surfaces 32 which are disposed between cutting edges 26. Alternatively, as shown in the embodiment of FIG. 8, needle body 12 may incorporate concave surfaces 34. Concave surfaces 34 may be formed through a conventional grinding process, e.g., a hollow grinding process, to extend between and define cutting edges 26. Concave surfaces 34 advantageously reduce required penetration and drag forces by presenting a reduced profile to the tissue during each pass.

The choice of materials of surgical needle 10 is made to optimize strength, ductility and resistance to bending or breaking of the needle. However, as noted, the cross-sectional shape and dimensions of the needle contributes significantly to the physical characteristics of the needle. Preferred materials include stainless steel such as series "300" stainless steels, which typically have tensile strengths of between 325,000-350,000 lbs/in.sup.2, attain their high strength from undergoing cold working as the material is converted from an ingot to wire of the desired diameter. "400" series stainless steel materials may also be utilized to form needle 10. Titanium, titanium alloys, biocompatible plastics are also envisioned.

Surgical needle 10 is manufactured through conventional cutting, coining, grinding and/or swaging processes, and may be heat treated to further enhance its strength and resistance to bending. A lubricious coating such as silicon may be applied to needle body to further enhance penetration and drag characteristics.

Sutures for attachment to surgical needle 10 include silk, nylon, linen, cotton, polyester, polypropylene, stainless steel, natural material such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical needle which comprises:
   a needle body including proximal and distal ends, and defining a longitudinal axis, the needle body including from distal to proximal:
   a hemispherical needle tip;
   a plurality of surfaces extending from the hemispherical needle tip, each of the surfaces being substantially planar; and
   a projecting element disposed between adjacent surfaces, the projecting element extending radially outwardly from the normal vertex formed by the intersection of the substantially planar surfaces with respect to the longitudinal axis and having an outer cutting edge, the outer cutting edge being coterminous with the hemispherical needle tip thereby leading to a smooth transition from the needle tip to the cutting edge wherein the adjacent surfaces define a first dimension transverse to the longitudinal axis to the needle body and the hemispherical needle tip define a second dimension transverse to the longitudinal axis greater than the first dimension.

2. The surgical needle according to claim 1 wherein the hemispherical needle tip defines a circular cross-sectional dimension.

3. The surgical needle according to claim 2 where the hemispherical needle tip defines a general elliptical cross-sectional dimension.

4. The surgical needle according to claim 1 wherein the outer cutting edges extend from the hemispherical needle tip toward the needle body.

5. The surgical needle according to claim 4 including at least four of the cutting edges.

6. The surgical needle according to claim 4 wherein the cutting edges each define a distal end and whereby an outer extent of the needle body inclusive of the distal ends of the cutting edges is substantially equivalent to an outer periphery of the hemispherical needle tip.

7. The surgical needle according to claim 4 wherein the cutting edges each define a distal end and whereby an outer extent of the needle body inclusive of the distal ends of the cutting edges is greater than an outer periphery of the hemispherical needle tip.

8. The surgical needle according to claim 1 including a suture attached to the proximal end of the needle body.

9. A surgical needle, which comprises:
   a needle body defining leading and trailing ends;
   a general spherical region disposed adjacent the leading end of the needle body, the spherical region defining a blunt outer surface; and
   a plurality of projecting elements extending contiguously from the spherical region toward the trailing end of the needle body, the plurality of projecting elements each having a generally triangular-shape formed from a wherein the adjacent surfaces define a first dimension transverse to the longitudinal axis to the needle body and the hemispherical needle tip define a second dimension transverse to the longitudinal axis greater than the first dimension pair of linear sides extending radially outward from the spherical region at oblique angles formed between adjacent planar side surfaces and the linear sides of the projecting elements, and having a cutting edge wherein the planar side surfaces define a first dimension transverse to the longitudinal axis to the needle body and the spherical region define a second dimension transverse to the longitudinal axis greater than the first dimension.

10. The surgical needle according to claim 9 wherein the cutting edges each define a leading end and whereby an outer extent of the needle body inclusive of the leading ends of the cutting edges is substantially equivalent to an outer periphery of the general spherical region.

11. The surgical needle according to claim 9 wherein the cutting edges each define a leading end and whereby an outer extent of the needle body inclusive of the leading ends of the cutting edges is greater than an outer periphery of the general spherical region.

\* \* \* \* \*